United States Patent
Matsumae et al.

[11] Patent Number: 5,883,264
[45] Date of Patent: Mar. 16, 1999

[54] PROCESS FOR PREPARING OPTICALLY ACTIVE TRANS-3-PHENYLGLYCIDAMIDE COMPOUNDS

[75] Inventors: Hiroaki Matsumae, Kobe; Akiko Idei, Akashi; Takuo Nishida, Amagasaki; Yasuhiko Ozaki, Neyagawa; Takeji Shibatani, Kobe, all of Japan

[73] Assignee: Tanabe Seiyaku Co., Ltd., Osaka, Japan

[21] Appl. No.: 812,778

[22] Filed: Mar. 6, 1997

[30] Foreign Application Priority Data

Mar. 15, 1996 [JP] Japan .................................. 8-058992

[51] Int. Cl.⁶ ...................... C07D 303/46; C07D 301/32
[52] U.S. Cl. .................. 549/548; 549/541; 549/552; 549/553
[58] Field of Search ..................... 549/539, 541, 549/548, 552, 553; 435/123

[56] References Cited

U.S. PATENT DOCUMENTS

| | | | |
|---|---|---|---|
| 4,341,718 | 7/1982 | Kim et al. ............... | 562/597 |
| 4,590,188 | 5/1986 | Takeda et al. ........... | 514/211 |
| 4,959,359 | 9/1990 | Mohacsi et la. ......... | 514/211 |
| 5,198,557 | 3/1993 | Giordano et al. ........ | 549/513 |
| 5,244,803 | 9/1993 | Morei et al. ............. | 435/280 |
| 5,283,193 | 2/1994 | Yamamoto et al. ..... | 435/280 |
| 5,571,704 | 11/1996 | Ghirotto et al. ........ | 435/123 |

FOREIGN PATENT DOCUMENTS 0417785  3/1991  European Pat. Off. .

*Primary Examiner*—Ba K. Trinh
*Attorney, Agent, or Firm*—Browdy and Neimark

[57] ABSTRACT

Process for preparing optically active trans-3-phenylglycidamide compound, which comprises subjecting racemic trans-3-phenylglycidamide compound of the formula (I)

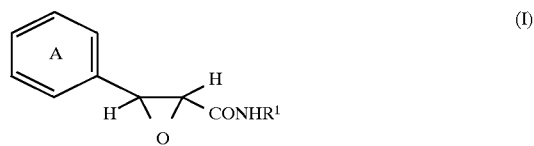

(I)

wherein Ring A is substituted or unsubstituted benzene, and $R^1$ is H or lower alkyl, to optical resolution using a microorganism having ability of preferentially hydrolyzing one of (2S,3R) isomer or (2R,3S) isomer thereof, and process for preparing an optically active 1,5-benzothiazepine derivative from the thus-obtained optically active trans-3-phenylglycidamide compound.

15 Claims, No Drawings

PROCESS FOR PREPARING OPTICALLY ACTIVE TRANS-3-PHENYLGLYCIDAMIDE COMPOUNDS

The present invention relates to a process for preparing an optically active trans-3-phenylglycidamide compound, and a process for preparing an optically active 1,5-benzothiazepine derivative with using the optically active trans-3-phenylglycidamide compound.

PRIOR ART

It is known that optically active 3-phenylglycidic acids or esters are useful as intermediates for preparing 1,5-benzothiazepine derivatives having various pharmacological activities such as coronary vasodilating activity, platelet aggregation inhibitory activity, etc. and being useful as medicaments (cf. U.S. Pat. No. 4,590,188).

It is also known that optically active 3-phenylglycidic acid ester compounds, especially (2S,3R) optically active isomer thereof can be prepared by permitting a culture broth, cells or treated cells of a microorganism having ability of asymmetrically hydrolyzing a (2R,3S)-3-phenylglycidic acid ester compound to act on the corresponding racemic 3-phenylglycidic acid ester compound, thereby hydrolyzing the (2R,3S) optically active isomer thereof, and isolating and collecting the unhydrolyzed (2S,3R) antipode from the reaction mixture (EP-A-0417785).

BRIEF DESCRIPTION OF THE INVENTION

The present inventors have intensively studied an improved process for preparing 1,5-benzothiazepine derivatives with using 3-phenylglycidamide compounds instead of 3-phenylglycidic acid esters, and they have also studied in order to obtain an improved process for preparing an optically active 3-phenylglycidamide compound from which 1,5-benzothiazepine derivatives can be obtained in the optically active form which is more desirable.

An object of the present invention is to provide a process for preparing an optically active trans-3-phenylglycidamide compound by treating the corresponding racemic trans-3-phenylglycidamide compound of the following formula (1):

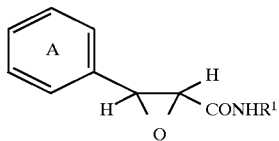

wherein Ring A is a substituted or unsubstituted benzene ring, and $R^1$ is a hydrogen atom or a lower alkyl group, with a microorganism having ability of preferentially hydrolyzing one of the optically active isomers thereof, and isolating and collecting the other antipode which is not hydrolyzed by said microorganism. Another object of the present invention is to provide a process for preparing an optically active 1,5-benzothiazepine derivative by using said optically active trans-3-phenylglycidamide compound.

DETAILED DESCRIPTION OF INVENTION

By the study of the present inventors, it has been found that the desired 1,5-benzothiazepine derivatives can be obtained by reacting a 3-phenylglycidamide compound with a 2-aminothiophenol derivative, and subjecting the product to intramolecular cyclization reaction (Japanese Patent Application No. 35302/1996). Further, the present inventors have found that some microorganisms show ability of preferentially hydrolyzing one of (2S,3R) isomer and (2R,3S) isomer of trans-3-phenylglycidamide compound, and that the desired optically active 3-phenylglycidamide compound can be prepared by treating racemic trans-3-phenylglycidamide compound with such microorganisms to hydrolyze one of the optical active isomers, followed by isolating and collecting the unhydrolyzed antipode from the reaction mixture, and they have accomplished the present invention.

According to the present invention, an optically active trans-3-phenylglycidamide compound of the formula (I):

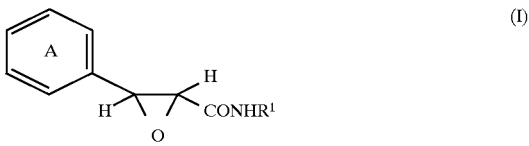

wherein Ring A is a substituted or unsubstituted benzene ring, and $R^1$ is a hydrogen atom or a lower alkyl group, is prepared by contacting racemic trans-3-phenylglycidamide compound of the formula (I) with a culture or treated culture of a microorganism having ability of preferentially hydrolyzing one of (2S,3R) isomer and (2R,3S) isomer thereof, followed by isolating and collecting the unhydrolyzed antipode from the reaction mixture.

The process of the present invention can be applied to any 3-phenylglycidamide compound of the formula (I) wherein Ring A is either an unsubstituted benzene ring or a benzene ring being substituted by a lower alkyl group, a lower alkoxy group or a halogen atom. The substituent on Ring A includes, for example, methyl group, methoxy group, etc. at the 4-position of the benzene ring The lower alkyl group for $R^1$ includes, for example, methyl group, ethyl group, isopropyl group or t-butyl group.

The starting racemic trans-3-phenylglycidamide compound (I) of the present invention includes not only a mixture of (2S,3R) isomer and (2R,3S) isomer at even ratio, but also mixtures of these isomers at any ratio.

The microorganisms used in the present invention include any microorganisms having ability of preferentially hydrolyzing one of (2S,3R) isomer and (2R,3S) isomer of the racemic trans-3-phenylglycidamide compounds (I), for example, microorganisms such as bacteria, yeasts, molds, etc. Suitable examples of the microorganisms are, bacteria belonging to the genus Comamonas, the genus Achromobacter, the genus Rhodococcus, the genus Arthrobacter, the genus Rhodobacter or the genus Flavobacterium, yeasts belonging to the genus Candida, the genus Rhodosporidium, the genus Cryptococcus, the genus Rhodotorula or the genus Yarrowia, and molds belonging to the genus Mucor, the genus Aspergillus, the genus Penicillium or the genus Aureobasidium.

Specific examples of such microorganisms may include, for example, bacteria such as *Comamonas acidovorans* ATCC 11299a, Ditto IFO 13582, *Achromobacter aquatilis* OUT 8003, *Rhodococcus sp.* ATCC 15592, *Arthrobacter paraffineus* ATCC 21219, *Rhodobacter sphaeroides* ATCC 21286, *Flavobacterium rigense* No. 35 (FERM BP-5289); yeasts such as *Candida maltosa* IAM 12247, Ditto JCM 1504, *Candida parapsilosis* IFO 0708, *Candida rugosa* IFO 0591, *Candida tropicalis* IFO 1401, *Rhodosporidium toruloides* IFO 0559, *Rhodotorula gulutinis* OUT 6152, *Rhodotorula rubra* OUT 6158, *Yarrowia lipolytica* IFO 0717, Ditto IFO 1209, *Cryptococcus laurentii* OUT 6027 (FERM P-14400); molds such as *Aspergillus oryzae* IFO 5710, *Aspergillus flavus* IFO 5839, *Mucor racemosus* IFO 6745,

*Mucor hiemalis* IFO 6753, Ditto OUT 1047, *Mucorjanssenii* OUT 1050, *Mucor circinelloides* IFO 6746, *Penicillium notatum* IFO 4640, *Aureobasidium pullulans* IFO 6405, etc. These microorganisms can be used either wild strains or mutant strains and those which are derived from these microorganisms according to the biotechnological manner such as gene recombination and cell fusion.

Examples of the medium for culturing the microorganisms include any medium in which the above-mentioned microorganisms can grow. For example, there can be preferably used a medium containing 0.4 to 15% of carbon sources (e.g. saccharide such as glucose, sucrose or molasses, organic acid such as fumaric acid or citric acid, or alcohol such as glycerol), and 0.3 to 2.0% of nitrogen sources (e.g. inorganic ammonium salt such as ammonium sulfate or ammonium chloride, urea, peptone, meat extract, corn-steep liquor, yeast extract or casein hydrolyzate). Moreover, if necessary, an appropriate amount of an inorganic salt such as phosphate, magnesium salt, potassium salt or calcium salt and a metal ion such as manganese or zinc may be also present in the medium. When a synthetic medium is employed, if necessary, it is effective to add, for example, an amino acid such as proline or histidine, biotin or thiamine, etc. In addition, if necessary, 0.1 of 2.0% of a vegetable oil, a racemic trans-3-phenylglycidamide compound (I) and a surfactant can be also added as an enzyme-inducing substance or a defoaming agent to enhance the enzyme activity. The medium is preferably employed with adjusting to pH 5 to 7.

Cultivation after inoculation of the microorganism onto the above-mentioned medium can be performed in a conventional manner such as shaking culture, aeration stirring culture, stationary culture and continuous culture.

Provided that the above-mentioned microorganisms can grow to produce amidase, the cultural conditions are not limited and may be selected suitably depending on the kind of the medium or the cultural method. Generally, it is desired to adjust the pH value of initial culture to 5 to 7, and carry out cultivation at room temperature or under heating, for example, at a temperature from 20° C. to 40° C.

The culture or treated culture of the microorganisms used in the present invention may be any one which can preferentially hydrolyze one of a (2R,3S) isomer and a (2S,3R) isomer of racemic trans-3-phenylglycidamide compounds (I). Examples of the culture include culture broth and viable cells, and the treated culture includes washed cells, dried cells, cultural supernatant, ground cells, self-digested product of cells, extract of cells of the above-mentioned microorganism, or partially purified or purified enzyme obtained therefrom according to a conventional method.

The viable cells or culture supernatant may be obtained by centrifugation or filtration of the culture broth which is prepared by culturing the microorganism as mentioned above. The washed cells are obtained by washing the viable cells with saline. The dried cells are obtained by subjecting viable cells or washed cells to lyophilization, or acetone-drying. The ground cells are obtained by treating viable cells or washed cells with various physicochemical methods, for example, ultrasonic treatment, french press, osmotic shock, freeze-thawing, grinding with alumina, treatment with a lytic enzyme, a surfactant, or an organic solvent, etc. The extract of cells is obtained, for example, removing the solid materials from ground cells by filtration, centrifugation, etc. The partially purified enzyme or purified enzyme is obtained, for example, by fractionating ground cells or culture supernatant by a conventional method (e.g. fractionation with ammonium sulfate, ion exchange chromatography or gel filtration chromatography, etc.), and purifying them with using as an index the ability of preferentially hydrolyzing one of (2R,3S) isomer and (2S,3R) isomer of the compound (I).

The above culture (viable cells, etc.) or treated culture of the present invention may be used without any further treatment, but may be also immobilized by known methods such as the methods using polyacrylamide, a sulfur-containing polysaccharide gel (e.g. carrageenan gel), an alginic acid gel or an agar gel, etc., before use. Further, an enzyme obtained by purification from the extract of microbial cells by combination of known methods can be also employed.

The preferential hydrolysis reaction of the racemic trans-3-phenylglycidamide compound (I) by the above-mentioned microorganisms is illustrated by the following scheme.

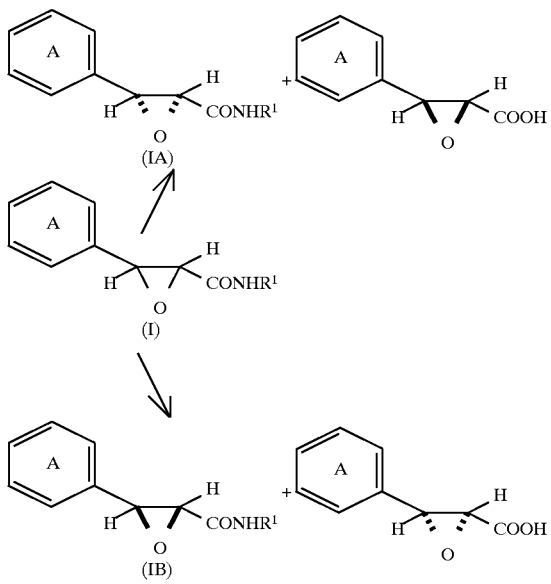

wherein Ring A and $R^1$ are the same as defined above.

That is, by using a microorganism having ability of preferentially hydrolyzing (2R,3S)-3-phenylglycidamide compound of racemic trans-3-phenylglycidamide compounds (I), there is obtained (2S,3R) optically active compound (IA). On the other hand, by using a microorganism having ability of preferentially hydrolyzing (2S,3R)-3-phenylglycidamide compound of racemic trans-3-phenylglycidamide compounds (I), there is obtained (2R,3S) optically active compound (IB).

According to the present process, the hydrolysis of the racemic trans-3-phenylglycidamide compounds (I) can be carried out by permitting the culture or the treated culture of the microorganism to contact with the racemic trans-3-phenylglycidamide compounds (I) and incubating the mixture.

The concentration of the substrate: racemic trans-3-phenylglycidamide compounds (I) may be generally 0.1 to 80% by weight, preferably 0.1 to 20% by weight, and the reaction can be carried out at room temperature or under heating, preferably at a temperature from 10° to 50° C., more preferably at a temperature from 20° to 40° C. During the reaction, it is preferable to adjust the pH value of the reaction mixture to 5 to 9, more preferably 6 to 8. As the reaction mixture, an aqueous solvent such as water, a mixture of water-dimethylformamide can be used, but from the standpoint of stabilization of the substrate, the reaction can be carried out in a two-phase solvent system of an aqueous solvent (e.g. water, etc.) and an organic solvent. The organic solvent includes, for example, aromatic hydrocarbons (e.g. toluene, xylene, chlorobenzene, etc.), halogenated or non-halogenated aliphatic hydrocarbons (e.g. isooctane, carbon tetrachloride, dichloromethane, trichloromethane, etc.), acetic acid esters (e.g. ethyl acetate, butyl acetate, etc.), ketones (e.g. methyl isobutyl ketone, acetone, etc.), ethers (e.g. t-butyl methyl ether, diisopropyl ether, etc.), alcohols (e.g. methyl alcohol, ethyl alcohol, n-propyl alcohol, isopropyl alcohol, n-butyl alcohol, t-butyl alcohol, etc.). Among these solvents, toluene, methyl isobutyl ketone, methanol, ethanol and carbon tetrachloride are more preferable.

When the reaction is carried out in the presence of a surfactant, the reaction is promoted so that the reaction time is shortened, and the yield of desired optically active trans-3-phenylglycidamide compounds is increased. The surfactant may be cetylpyridinium bromide, cetyltrimethylammonium bromide, polyethylene glycol, polyoxyethylene octylphenyl ether, etc., and the amount of the surfactant is preferably in the range from about 0.0001 to about 0.1% by weight based on the reaction mixture.

The optically active trans-phenylglycidamide compound obtained by the above hydrolysis can be readily isolated from the reaction mixture by a conventional method. For example, when the hydrolysis is carried out in an aqueous solvent system such as water-dimethylformamide, one of the optically active trans-3-phenylglycidamide compound is hydrolyzed and then decarboxylated to be converted into an aldehyde compound, which can be further changed into a water soluble adduct by adding thereto sodium hydrogen sulfite. On the other hand, the unhydrolyzed optically active antipode is hardly soluble in water, and therefore, the desired optically active trans-3-phenylglycidamide compound can be isolated as crystals from the reaction mixture after hydrolysis by extracting it with an organic solvent such as ethyl acetate, and concentrating under reduced pressure.

When the hydrolysis is carried out in a two-phase solvent system of a water-organic solvent, one of the optically active trans-3-phenylglycidamide compound is hydrolyzed and migrated into the aqueous layer, while the unhydrolyzed optically active antipode compound remains in the organic solvent, and therefore, the desired optically active compound can be isolated from the reaction mixture after the hydrolysis by collecting the organic layer and concentrating under reduced pressure.

The optically active trans-3-phenylglycidamide compound (IB) or (IA) thus obtained can be converted into the corresponding (2S,3S)-1,5-benzothiazepine derivative of the formula (III):

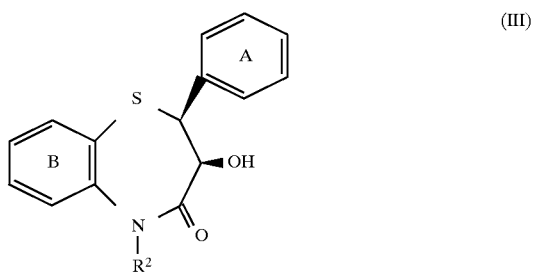

wherein Ring B is a substituted or unsubstituted benzene ring, $R^2$ is a hydrogen atom or a di-lower alkylamino-lower alkyl group and Ring A is the same as defined above, or the corresponding (2R,3R)-1,5-benzothiazepine derivative of the formula (IV):

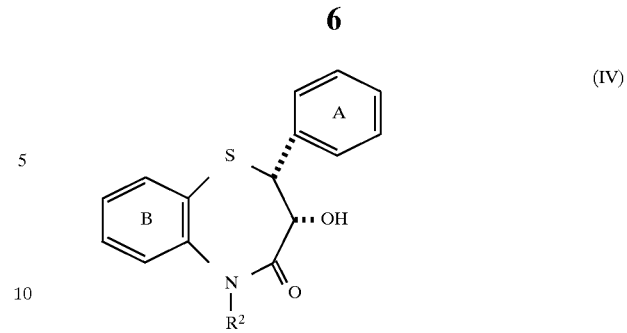

wherein Ring A, Ring B and $R^2$ are the same as defined above, respectively, by reacting it with a 2-aminothiophenol derivative of the formula (II):

wherein Ring B and $R^2$ are the same as defined above, followed by subjecting the product to intramolecular cyclization reaction.

The reaction of the (2S,3R)-3-phenylglycidamide compound (IA) or the (2R,3S)-3-phenylglycidamide compound (IB) with the 2-aminothiophenol derivative (II) can be carried out in the presence or absence of an appropriate iron catalyst (e.g. iron sulfate, etc.) in an organic solvent (e.g. xylene, etc.). The subsequent intramolecular cyclization reaction can be carried out in the presence or absence of an acid (e.g. methanesulfonic acid, etc.) in an organic solvent (e.g. xylene, etc.) at a temperature from 0° to 250° C.

Ring B of the 2-aminothiophenol derivative (II) used in the above reaction is a benzene ring which may optionally have a substituent selected from a lower alkyl group and a halogen atom. The di-lower alkylamino-lower alkyl group for $R^2$ is, for example, dimethylaminomethyl group, 2-(dimethylamino)ethyl group, etc.

The starting racemic trans-3-phenylglycidamide compound (I) can be prepared, for example, by the method disclosed in U.S. Pat. No. 4,959,359, etc.

That is, racemic trans-3-phenylglycidamide compound (I) is prepared by reacting a glycidic acid ester compound of the formula (VII):

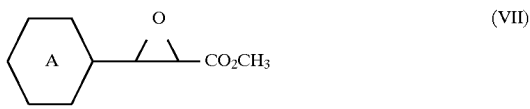

wherein Ring A is the same as defined above, with a compound of the formula (VIII)

wherein $R^1$ is the same as defined above, in an appropriate solvent (e.g. methanol, tetrahydrofuran, dimethylformamide, toluene, xylene, etc.), at a temperature from 0° to 100° C.

Throughout the claims and specification, the lower alkyl group means a $C_1$–$C_6$ alkyl group and the lower alkoxy group means a $C_1$–$C_6$ alkoxy group.

EFFECTS OF THE INVENTION

According to the process of the present invention, an optically active trans-3-phenylglycidamide compound can be obtained as crystals of high purity from the corresponding racemic trans-3-phenylglycidamide compounds in a single step. Therefore, the process of the present invention can be an industrially advantageous process for preparing the optically active trans-3-phenylglycidamide compounds. Besides, according to the present invention, an optically active 1,5-benzothiazepine derivative, which is useful as a medicament, can easily be prepared by using the optically active trans-3-phenylglycidamide compound. Therefore, the process of the present invention is also useful for preparing optically active 1,5-benzothiazepine derivatives on an industrial scale.

EXAMPLES

The present invention is illustrated by the following Examples and Reference Examples, but should not be construed to be limited thereto.

Example 1

An amidase producing medium (3 ml) (components: 2% of monosodium fumarate; 1% of yeast extract; 0.2% of ammonium chloride; 0.2% of dipotassium phosphate; 0.02% of magnesium sulfate. heptahydrate; 0.003% of iron sulfate. heptahydrate; 0.1% of sodium chloride; 0.1% of ε-caprolactam; pH 7.0) is charged into a test tube (13 mm φ×120 mm), and sterilized at 120° C. for 10 minutes. Into the medium is inoculated a platinum loop of various microorganisms as listed in Table 1, and cultivation (shaking culture) is carried out at 30° C. for 24 hours (for bacteria), or for two days (for yeast), with shaking at 300 rpm.

To the culture broth (2.9 ml) thus obtained are added 1.0M Tris-HCl buffer (pH 7.0, 0.3 ml) and a solution (0.075 ml) of racemic trans-3-(4-methylphenyl)glycidamide (hereinafter, referred to as racemic trans-MPGA, 40 mg/ml) in dimethylformamide (DMF) (the total amount of racemic trans-MPGA; 3 mg), and the mixture is subjected to hydrolysis with shaking at 300 rpm at 30° C. for 24 hours.

The remaining amount (mg) of optically active MPGA in each reaction solution is determined in the following manner.

Ethyl acetate (3 ml) is added to the reaction solution to extract MPGA. The ethyl acetate layer (100 μl) is collected and added into a mixture (2.9 ml) of n-hexane and isopropanol (15:1). This sample is analyzed by high performance liquid chromatography (HPLC) of CHIRALCEL OB-H (4.6 mm φ×250 mm, manufactured by Daicel Chemical Industries, Ltd.) and the remaining amounts of (2R,3S)-MPGA and (2S,3R)-MPGA in the reaction solution are determined. HPLC is carried out by using as a solvent a mixture of n-hexane:isopropanol (15:1) at a flow rate of 1 ml/min. at 40° C.

The results are shown in Table 1. In Table 1, "Blank" means the amount of optically active MPGA in the reaction solution wherein the same procedures were carried out without a culture broth of microorganism.

TABLE 1

| Microorganisms | The remaining amount of optically active MPGA (mg) | |
|---|---|---|
| | (2S, 3R) isomer | (2R, 3S) isomer |
| Blank | 1.28 | 1.28 |
| Bacterium | | |
| Comamonas acidovorans | 0.87 | <0.01 |

TABLE 1-continued

| Microorganisms | The remaining amount of optically active MPGA (mg) | |
|---|---|---|
| | (2S, 3R) isomer | (2R, 3S) isomer |
| ATCC 11299 a | | |
| Achromobacter aquatilis OUT 8003 | 0.35 | 1.23 |
| Rhodococcus sp. ATCC 15592 | 0.03 | 1.17 |
| Arthrobacter paraffineus ATCC 21219 | 0.23 | 1.28 |
| Rhodobacter sphaeroides ATCC 21286 | 0.98 | 1.28 |
| Flavobacterium rigense NO. 35 (FERM BP-5289) | 0.84 | 1.28 |
| Yeast | | |
| Candida maltosa IAM 12247 | 0.17 | 0.91 |
| Candida maltosa JCM 1504 | 0.83 | 1.15 |
| Candida parapsilosis IFO 0708 | 0.14 | 0.92 |
| Candida rugosa IFO 0591 | 0.18 | 1.04 |
| Candida tropicalis IFO 1401 | 0.37 | 0.95 |
| Rhodosporidium toruloides IFO 0559 | 0.57 | 0.89 |
| Rhodotorula gulutinis OUT 6152 | 0.23 | 0.09 |
| Rhodotorula rubra OUT 6158 | 0.51 | 0.90 |
| Yarrowia lipolytica IFO 0717 | 0.82 | 1.03 |
| Yarrowia lipolytica IFO 1209 | 0.77 | 0.95 |

Example 2

Using the same amidase producing medium (pH 6.0) as used in Example 1 except that 3% glucose is used instead of 2% monosodium fumarate, the microorganisms as listed in Table 2 are cultured. The incubation is carried out for three days (for molds), or for two days (for yeast).

To the culture broth thus obtained (3.0 ml) are added 1.0M Tris-HCl buffer (pH 7.0, 0.3 ml) and a solution (0.075 ml) of racemic trans-MPGA (40 mg/ml) in DMF, and the mixture is subjected to hydrolysis at 30° C. for 24 hours with shaking at 300 rpm.

The remaining amount (mg) of the optically active MPGA in each reaction solution is determined in the same manner as in Example 1. The results are shown in Table 2.

TABLE 2

| Microorganisms | The remaining amount of optically active MPGA (mg) | |
|---|---|---|
| | (2S, 3R) isomer | (2R, 3S) isomer |
| Blank | 1.28 | 1.28 |
| Mold | | |
| Aspergillus oryzae IFO 5710 | 0.48 | 1.01 |
| Aspergillus flavus IFO 5839 | 0.30 | 0.81 |
| Mucor racemosus, IFO 6745 | 1.28 | 0.64 |
| Mucor hiemalis OUT 1047 | 1.32 | 0.18 |
| Mucor janssenii OUT 1050 | 1.48 | 1.12 |
| Mucor circinelloides IFO 6746 | 1.31 | 1.00 |
| Mucor hiemalis IFO 6753 | 1.38 | 0.85 |
| Pencillium notatum IFO 4640 | 0.32 | 0.86 |
| Aureobasidium pullulans IFO 6405 | 0.59 | 1.22 |
| Yeasts | | |
| Cryptococcus laurentii OUT 6027 (FERM P-14400) | 1.08 | 1.33 |

Example 3

Comamonas acidovorans ATCC 11299a is cultured by using 500 ml volume shaking flasks (20 flasks) wherein the same amidase producing medium (100 ml) as used in Example 1 is charged, at 30° C. with shaking at 140 rpm for 24 hours. To the culture broth are added 1M phosphate buffer (pH 7, 10 ml) and a solution of racemic trans-MPGA (100 mg) in DMF (1 ml), and the reaction mixture is incubated at 30° C. with shaking at 140 rpm (total amount of substrate: 2 g/20 flasks). After reaction for 1.5 hour, all reaction mixtures are combined, and thereto is added acetone (6 liters; the three-fold volume of the reaction mixture). The mixture is stirred for 10 minutes to give acetone dried cells. The cells thus obtained are removed by filtration with using celite. The filtrate is concentrated under reduced pressure to remove the acetone, and the aqueous layer containing (2S,3R)-MPGA is extracted with ethyl acetate (1.5 liter). The ethyl acetate layer is washed successively with sodium sulfite solution (pH 6.4, 600 ml), a saturated aqueous sodium chloride solution (600 ml), an aqueous sodium hydrogen carbonate solution (pH 7–9), and a saturated aqueous sodium chloride solution (500 ml×3).

The ethyl acetate layer is dried over anhydrous magnesium sulfate, and concentrated under reduced pressure. The resulting solid is dissolved in toluene (200 ml) at 90° C. The solution is allowed to stand at room temperature for one hour, and then further allowed to stand at 4° C. for more than two hours. The precipitated (2S,3R)-MPGA crystals are collected by filtration.

| Yield of recrystallization: | |
|---|---|
| First crystals | 647 mg |
| Second crystals | 99.7 mg |
| Third crystals | 15.1 mg |
| Totally | 761.8 mg |

Isolation yield (%) of optically active compound: 76%
The results of mechanical analysis:
 IR (KBr) vmax: 3402.2 cm$^{-1}$, 3200 cm-$^{1}$, 1640 cm$^{-1}$
 NMR (DMSO): 2.30 (s, 3H), 3.47 (d, 1H, J=1.9Hz), 3.97 (d, 1H, J=1.9Hz), 7.15–7.33 (4H), 7.42 and 7.57 (s×2, 1H×2) MS (m/z): 177 (M$^+$) Optical purity: 100% e.e. (analysis by HPLC using CHIRALCEL OB-H) M.p. 176.5°–177.5° C. Optical rotation: $[\alpha]_D^{26}$=+158° (c=0.50, methanol)

Example 4

In the same manner as in Example 3, *Comamonas acidovorans* ATCC 11299a is cultured with shaking in the amidase producing medium for 24 hours. To the culture broth are added 1M phosphate buffer (pH 7, 10 ml) and a solution (1 ml) of racemic trans-MPGA (100 mg) in DMF, and the mixture is incubated with shaking at 140 rpm at 30° C. Each 2 ml of the reaction solution is collected at constant intervals, and the MPGA therein is extracted with the same volume of ethyl acetate. The remaining amount of optically active MPGA in each sample is determined by HPLC analysis using CHIRALCEL OB-H.

The reaction is carried out on two reaction systems, i.e. Lot A and Lot B, and the change with time of the remaining amount of (2S,3R)-MPGA and (2R,3S)-MPGA in each Lot is shown in Tables 3 and 4. In Tables 3 and 4, the hydrolysis ratio (%) of the racemic trans-MPGA, and the optical purity of (2S,3R)-MPGA are also indicated. The hydrolysis ratio (C) (%) is calculated according to the following equation.

$$C\ (\%) = \left(1 - \frac{A+B}{A_0+B_0}\right) \times 100$$

$A_0+B_0$: The amount of racemic MPGA added as a substrate
A: The remaining amount of (2S,3R)-MPGA
B: The remaining amount of (2R,3S)-MPGA

TABLE 3

The results in Lot A

| Reaction time (h) | The remaining ratio of (2S, 3R)-MPGA (%) | The remaining ratio of (2R, 3S)-MPGA (%) | Hydrolysis ratio (%) | Optical purity (e.e. %) |
|---|---|---|---|---|
| 0 | 100 | 100 | 0 | 0 |
| 1 | 94.7 | 0 | 52.7 | >99.9 |
| 3 | 85.6 | 0 | 57.2 | >99.9 |

TABLE 4

The results in Lot B

| Reaction time (h) | The remaining ratio of (2S, 3R)-MPGA (%) | The remaining ratio of (2R, 3S)-MPGA (%) | Hydrolysis ratio (%) | Optical purity (e.e. %) |
|---|---|---|---|---|
| 0 | 100 | 100 | 0 | 0 |
| 1 | 100 | 0 | 50 | >99.9 |
| 3 | 87.3 | 0 | 56.4 | >99.9 |

Example 5
Hydrolysis of racemic trans-3-(4-methoxyphenyl) glycidamide (racemic trans-MeOPGA):
 To an amidase producing medium (components; 2% of monosodium fumarate; 1% of yeast extract; 0.2% of ammonium chloride; 0.2% of dipotassium phosphate; 0.02% of magnesium sulfate·heptahydrate; 0.003% of iron sulfate·heptahydrate; 0.1% sodium chloride; 0.1% of ε-caprolactam, pH 7) is inoculated *Comamonas acidovorans* ATCC 11299a, and the mixture is incubated at 30° C. with shaking at 300 rpm for 42 hours.

To the culture broth (2.2 ml) are added 0.4M Tris-HCl buffer (pH 7, 8 or 9, each 0.75 ml) and a solution (0.05 ml) containing racemic trans-MeOPGA (3 mg) in DMF, and the mixture is incubated at 30° C. with shaking at 300 rpm for 25 minutes.

The MeOPGA in the reaction solution is extracted with ethyl acetate (3 ml), and analyzed by HPLC using CHIRAL-CEL OD. The remaining ratio of (2S,3R)-MeOPGA and (2R,3S)-MeOPGA is shown in Table 5.

TABLE 5

| pH 7 | | pH 8 | | pH 9 | |
|---|---|---|---|---|---|
| (2S, 3R)-isomer | (2R, 3S)-isomer | (2S, 3R)-isomer | (2R, 3S)-isomer | (2S, 3R)-isomer | (2R, 3S)-isomer |
| 44.2 | 37.2 | 48.6 | 40.2 | 55.4 | 44.4 |

Conditions for HPLC analysis:
  Column: CHIRALCEL OD
  Flow rate: 1.0 ml/min.
  Temperature: 40° C.
  Detection: 235 nm
  Solvent: n-Hexane: isopropanol=20: 1

Example 6

Microorganism producing (2S,3R)-3-(4-methylphenyl) glycidamide ((2S,3R)-MPGA):

To a 500 ml shaking flask containing an amidase producing medium (100 ml/flask, components: 2% of monosodium fumarate; 1% of yeast extract; 0.2% of ammonium chloride; 0.2% of dipotassium phosphate; 0.02% of magnesium sulfate·heptahydrate; 0.003% of iron sulfate·heptahydrate; 0.1% of sodium chloride; 0.1% of ε-caprolactam, pH 7) is inoculated *Comamonas acidovorans* IFO 13582, and the mixture is incubated at 30° C. with shaking at 140 rpm for 24 hours.

To the culture broth are added 1M phosphate buffer (pH 7, 10 ml) and a solution (1 ml) containing racemic trans-MPGA (100 mg) in DMF, and the mixture is incubated at 30° C. with shaking at 140 rpm for 6 hours.

The MPGA in the reaction solution (2 ml) is extracted with ethyl acetate (2 ml), and analyzed by HPLC using CHIRALCEL OB-H. The remaining ratio of (2S,3R)-MPGA and (2R,3S)-MPGA is shown in Table 6.

TABLE 6

| Reaction time (h) | Remaining ratio of (2S, 3R)-isomer (%) | Remaining ratio of (2R, 3S)-isomer (%) | Hydrolysis ratio (%) | Optical purity (e.e. %) |
|---|---|---|---|---|
| 6 | 90.5 | 8.8 | 50.3 | 82.3 |

Conditions for HPLC analysis:

| Column: | CHIRALCEL OB-H |
| Flow rate: | 1.0 ml/min. |

| Temperature: | 40° C. |
| Detection: | 235 nm |
| Solvent: | n-Hexane:isopropanol = 15:1 |

Reference Example 1

(1) A mixture of (2R,3S)-3-(4-methoxyphenyl)glycidamide (1.93 g) and xylene (15 ml) is refluxed under nitrogen atmosphere. To the reaction solution is added a solution of 2-aminothiophenol (1.38 g) and iron sulfate·heptahydrate (0.28 mg) in methanol (0.2 ml) immediately after the refluxing starts. After reaction at the same temperature for 5 minutes, the reaction solution is cooled to room temperature. The reaction solution is subjected to HPLC analysis to confirm the production of 3-(2-aminophenylthio)-2-hydroxy-3-(4-methoxyphenyl) propionamide (2.69 g) (threo/erythro=91/9). The reaction solution is concentrated under reduced pressure to remove the solvent, and the residue thus obtained is dissolved with heating in ethanol (3 ml) and water (3 ml). The solution is gradually cooled with stirring to 0° C. for crystallization. The precipitated crystals are collected by filtration. The collected crystals are washed with iced 50% ethanol, and dried at 50° C. to give (2S,3S)-3-(2-aminophenylthio)-2-hydroxy-3-(4-methoxyphenyl) propioamide (0.84 g).

M.p. 110°–112° C. $[\alpha]_D^{25}$:+506° (c=1.0, methanol)

Conditions for HPLC analysis:

| Column: | WATERS PURESIL 5 μ C18 120 Å (4.6 × 150 mm), manufactured by Waters, Inc. |
| Solvent: | Acetonitrile: 10 mM potassium dihydrogen phosphate (pH 3) = 30:70 |
| Flow rate: | 1.0 ml/min. |
| UV Detection: | 254 nm |
| Temperature: | 40° C. |

(2) A mixture of (2S,3S)-3-(2-aminophenylthio)-2-hydroxy-3-(4-methoxyphenyl)propioamide (1.59 g), xylene (8 ml) and methanesulfonic acid (24 ml) is refluxed for 11 hours. The reaction solution is allowed to cool to room temperature with stirring. The precipitated crystals are collected by filtration, washed with cold methanol, and dried at 50° C. to give (2S,3S)-2,3-dihydro-3-hydroxy-2-(4-methoxyphenyl)-1,5-benzothiazepine-4(5H)-one (1.41 g).

M.p. 203°–205° C. $[\alpha]_D^{25}$:+114.3° (c=0.5, dimethylformamide) $^1$H-NMR (DMSO-d$_6$, δ): 3.76 (3H, s), 4.30 (1H, dd), 4.74 (1H, d), 5.05 (1H, d), 6.87–7.62 (8H, m), 10.32 (1H, s) Optical purity by HPLC: >99.9 e.e. %

Conditions for HPLC analysis:

| Column: | CHIRALCEL OD (4.6 × 150 mm), manufactured by Daicel Chemical Industries, Ltd. |

| Solvent: | n-Hexane:ethanol = 85:15 |
|---|---|
| Flow rate: | 0.5 ml/min. |
| UV detection: | 254 nm |
| Temperature: | 35° C. |

Reference Example 2

(1) (2S,3R)-3-(4-Methylphenyl)glycidamide and 2-amino-5-methylthiophenol are treated in the same manner as in Reference Example 1-(1) to give (2R,3R)-3-(2-amino-5-methylphenylthio)-2-hydroxy-3-(4-methylphenyl)-propionamide. M.p. 145°–146° C. $[\alpha]_D^{25}$:–410° (c=1, methanol)

(2) (2R,3R)-3-(2-Amino-5-methylphenylthio)-2-hydroxy-3-(4-methylphenyl)-propionamide is treated in the same manner as in Reference Example 1-(1) to give (2R,3R)-2,3-dihydro-3-hydroxy-2-(4-methylphenyl)-8-methyl-1,5-benzothiazepine-4(5H)-one.
M.p. 212°–214° C. $[\alpha]_D^{25}$:–129.2° (c=1, dimethylformamide) $^1$H-NMR (DMSO-$d_6$, δ): 2.29 (3H, s), 4.29 (1H, dd), 4.67 (1H, d), 5.03 (1H, d), 7.02–7.42 (7H, m), 10.20 (1H, s).

What is claimed is:

1. A process for preparing an optically active trans-3-phenyl-glycidamide compound, which comprises contacting a racemic trans-3-phenyl-glycidamide compound of the formula (I):

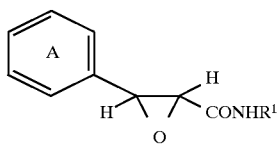

(I)

wherein Ring A is a substituted or unsubstituted benzene ring, and $R^1$ is a hydrogen atom or a lower alkyl atom group, with a culture or a treated culture of an amidase-producing microorganism having ability of preferentially hydrolyzing one of a (2S,3R) isomer or a (2R,3S) isomer of said racemic compound (I) to hydrolyze one of these isomers, and isolating and collecting the unhydrolyzed optical active antipode from the reaction mixture.

2. A process according to claim 1, wherein the microorganism is a member selected from bacteria belonging to the genus Comamonas, the genus Achromobacter, the genus Rhodococcus, the genus Arthrobacter, the genus Rhodobacter or the genus Flavobacterium; yeasts belonging to the genus Candida, the genus Rhodosporidium, the genus Cryptococcus, the genus Rhodotorula or the genus Yarrowia; and molds belonging to the genus Mucor, the genus Aspergillus, the genus Penicillium or the genus Aureobasidium.

3. A process according to claim 2, wherein the microorganisms is a member selected from Comamonas acidovorans, Achromobacter aquatilis, Rhodococcus sp., Arthrobacter paraffineus, Rhodobacter sphaeroides, Flavobacterium rigense, Candida maltosa, Candida parapsilosis, Candida rugosa, Candida tropicalis, Rhodosporidium toruloides, Rhodotorula gulutinis, Rhodotorula rubra, Cryptococcus laurentii, Yarrowia lipolytica, Aspergillus oryzae, Aspergillus flavus, Mucor racemosus, Mucor hiemalis, Mucor janssenii, Mucor circinelloides, Penicillium notatum and Aureobasidium pullulans.

4. A process according to claim 1, wherein the microorganism has ability of preferentially hydrolyzing a (2R,3S) isomer of the trans-3-phenylglycidamide compound (I).

5. A process according to claim 1, wherein the microorganism has ability of preferentially hydrolyzing a (2S,3R) isomer of the trans-3-phenylglycidamide compound (I).

6. A process according to claim 4, wherein the (2R,3S) isomer of the trans-3-phenylglycidamide compound (I) is (2R,3S)-3-(4-methylphenyl)-glycidamide.

7. A process according to claim 5, wherein the (2S,3R) isomer of the trans-3-phenylglycidamide compound (I) is (2S,3R)-3-(4-methoxyphenyl)-glycidamide.

8. A process according to claim 1, wherein Ring A of the racemic trans-3-phenylglycidamide compound (I) is a benzene ring which may optionally be substituted by a group selected from a lower alkyl group, a lower alkoxy group and a halogen atom.

9. A process according to claim 2, wherein the microorganism has ability of preferentially hydrolyzing a (2R, 3S) isomer of the trans-3-phenylglycidamide compound (I).

10. A process according to claim 3, wherein the microorganism has ability of preferentially hydrolyzing a (2R, 3S) isomer of the trans-3-phenylglycidamide compound (I).

11. A process according to claim 2, wherein the microorganism has ability of preferentially hydrolyzing a (2S, 3R) isomer of the trans-3-phenylglycidamide compound (I).

12. A process according to claim 3, wherein the microorganism has ability of preferentially hydrolyzing a (2S, 3R) isomer of the trans-3-phenylglycidamide compound (I).

13. A process according to claim 1, wherein Ring A of the racemic trans-3-phenylglycidamide compound (I) is a benzene ring which is substituted by a group selected from a lower alkyl group, a lower alkoxy group and a halogen atom.

14. A process according to claim 1 wherein said microorganism is Comamonas acidovorans.

15. A process for preparing an optically active trans-3-phenyl-glycidamide compound, which comprises contacting a racemic trans-3-phenyl-glycidamide compound of the formula (I):

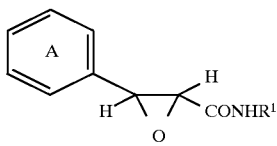

(I)

wherein Ring A is a substituted or unsubstituted benzene ring, and $R^1$ is a hydrogen atom or a lower alkyl atom group, with an amidase having ability of preferentially hydrolyzing one of a (2S,3R) isomer or a (2R,3S) isomer of said racemic compound (I) to hydrolyze one of these isomers, said amidase being produced by a microorganism selected from the group consisting of Comamonas acidovorans, Achromobacter aquatilis, Rhodococcus sp., Arthrobacter paraffineus, Rhodobacter sphaeroides, Flavobacterium rigense, Candid maltosa, Candida parapsilosis, Candida rugosa, Candida tropicalis, Rhodosporidium toruloides, Rhodotorula gulutinis, Rhodotorula rubra, Cryptococcus laurentii, Yarrowia lipolytica, Aspergillus oryzae, Aspergillus flavus, Mucor racemosus, Mucor hiemalis, Mucor janssenii, Mucor circinelloides, Penicillium notatum and Aureobasidium pullulans; and isolating and collecting the unhydrolyzed optical active antipode from the reaction mixture.

* * * * *